United States Patent [19]

Nakajima et al.

[11] Patent Number: 5,322,782
[45] Date of Patent: Jun. 21, 1994

[54] METHOD OF SYNTHESIZING OPTICALLY ACTIVE β-HALOLACTIC ACID

[75] Inventors: Hiroshi Nakajima; Masaaki Onda; Ryoichi Tsurutani; Kenzo Motosugi, all of Kyoto, Japan

[73] Assignee: Unitika Ltd., Hyogo, Japan

[21] Appl. No.: 963,255

[22] Filed: Oct. 19, 1992

Related U.S. Application Data

[63] Continuation of Ser. No. 424,632, Oct. 20, 1989, abandoned.

[30] Foreign Application Priority Data

Oct. 20, 1988 [JP] Japan ................. 63-265838

[51] Int. Cl.$^5$ ............ C12P 7/42; C12P 7/56; C12P 17/02; C12P 41/00
[52] U.S. Cl. .................. 435/146; 435/123; 435/139; 435/183; 435/195; 435/280; 435/877
[58] Field of Search ........... 435/123, 139, 146, 195, 435/280, 183, 877

[56] References Cited

U.S. PATENT DOCUMENTS 4,247,641 1/1981 Neidleman et al. ........... 435/123
4,284,723 8/1981 Neidleman et al. ........... 435/123
4,758,518 7/1988 Taylor ..................... 435/195 X
4,943,528 7/1990 Nakamura et al. ........... 435/158

FOREIGN PATENT DOCUMENTS 0179603 4/1986 European Pat. Off. .
0206436 12/1986 European Pat. Off. .
173598 7/1988 Japan ..................... 435/146

OTHER PUBLICATIONS

Biotechnology and Bioengineering, vol. 26, Jul. 1984, pp. 805–806.
Chemical Abstracts, vol. 97, 1982, p. 227, abstract No. 35149k.
Biological Abstracts, vol. 75, No. 10, 1983, p. 7807, abstract No. 75052.

*Primary Examiner*—Herbert J. Lilling
*Attorney, Agent, or Firm*—Sughrue, Mion, Zinn, Macpeak & Seas

[57] ABSTRACT

Optically active β-halolactic acids can be produced by contacting an α,β-dihalopropionic acid with 2-halo acid dehalogenase. When the pH of the reaction system is above 9, this process gives optically active glycidic acid. Treatment of the optically active β-halolactic acid thus obtained with an alkali also gives optically active glycidic acid.

9 Claims, No Drawings

METHOD OF SYNTHESIZING OPTICALLY ACTIVE β-HALOLACTIC ACID

This is a continuation of application Ser. No. 07/424,632 filed Oct. 20, 1989, now abandoned.

FIELD OF THE INVENTION

This invention relates to an efficient method of synthesizing an optically active β-halolactic acid or optically active glycidic acid, each valuable as an intermediate in the synthesis of medicinal chemicals.

BACKGROUND OF THE INVENTION

β-Halolactic acids and glycidic acid are important as intermediates in synthesizing a variety of drugs, for example leukotriens, prostaglandins, β-adrenal blockers and carnitine. In the past, most synthetic drugs were used in their racemic form, not in their optically active form. In recent years, however, several drugs have been found to be pharmacologically effective only in their optically active form while, when in racemic form, they are pharmacologically ineffective. Currently, there is an increasing tendency toward the synthesis of optically active compounds in the search for pharmacologically effective compounds. As is well known in the art, however, it is very difficult to synthesize optically active compounds by conventional methods of organic synthesis, which generally give only racemic products.

In producing optically active synthetic drugs, it is a frequent practice to produce or separate an optically active compound in an intermediate step of the synthesis and derive the final product drug therefrom. This is also the case with β-halolactic acids and glycidic acid, which are important intermediates in drug synthesis, and attempts have been made to produce optically active β-halolactic acids and optically active glycidic acid. Thus, for instance, in a process [process (a)] reported by Hirschbein et al. [B. L. Hirschbein and G. M. Whitesides: J. Am. Chem. Soc., 104, 4458 (1982)], optically active glycidic acid is synthesized by reducing chloropyruvic acid in the presence of lactate dehydrogenase and treating the resulting β-chlorolactic acid with potassium hydroxide for cyclization.

In another process [process (b)] reported by Ohashi et al. [T. Ohashi and J. Hasegawa: Yuki Gosei Kagaku Kyokai Shi (J. Synth. Org. Chem., Japan), 45, 331 (1987); JP-A-61-268197 (the term "JP-A" as used herein means an "unexamined published Japanese patent application"); J. Ferment. Technol., 64, 251 (1986)], 3-chloro-1,2-propanediol is microbially oxidized, followed by cyclization by treatment with potassium hydroxide, as described by Hirschbein et al.

It is also generally known that 2-halo acid dehalogenase catalyzes the conversion of an L-2-halo acid to the corresponding D-hydroxy acid [J. Biol. Chem., 243, 428 (1968); J. Eur. Biochem., 21, 99 (1971); Agric. Biol. Chem., 46, 837 (1982); JP-A-57-125690 and JP-A-57-125691]. In particular, the production of D-lactic acid from L-chloropropionic acid can be an effective method of producing optically active lactic acid from an industrial viewpoint.

Another method known for the production of optically active lactic acid starts with racemic chloropropionic acid and uses 2-halo acid dehalogenase which acts on both L-2-halo acid and D-2-halo acid (JP-A-59-31690). It is unknown whether an α,β-dihalopropionic acid, which is halogenated not only on the α-position carbon atom but also on the β-position carbon atom, can undergo dehalogenation only on the α-position carbon atom.

The above process (a) is disadvantageous in that an expensive coenzyme, namely NADH, must be used. Therefore, that process cannot become a commercial method for synthesizing an optically active β-halolactic acid or optically active glycidic acid. To overcome this drawback, a method which used glucose-6-phosphate dehydrogenase or, in other words, a coenzyme reproduction system in conjugation, has been proposed. However, this method has so far failed to produce satisfactory economic effects and, furthermore, is disadvantageous in that the two enzymes and the coenzyme NADH coexist in the reaction system, rendering the reaction system very complicated.

Process (b) does not involves the coenzyme regeneration problem but is disadvantageous in that the yield is as low as 10 to 28%.

In conclusion, none of the known processes or methods can be said to be a commercially advantageous way of producing an optically active β-halolactic acid or optically active glycidic acid.

While, as mentioned above, it is known that 2-halo acid dehalogenase acts on 2-halo acids to cause the dehalogenation, the prior art teaches nothing about the selective dehalogenation of α,β-dihalopropionic acids at the α-position.

SUMMARY OF THE INVENTION

The present inventors made intensive investigations in an attempt to provide a method of synthesizing an optically active β-halolactic acid or optically active glycidic acid at low cost, in an industrially advantageous manner and with high optical purity, and as a result, found that their objects could be realized when 2-halo acid dehalogenase is used in synthesizing optically active β-halolactic acids or optically active glycidic acid starting with α,β-dihalopropionic acids. The present invention was completed based on this finding.

The invention thus provides a method of synthesizing optically active β-halolactic acids which comprises causing 2-halo acid dehalogenase to act on an α,β-dihalopropionic acid; a method of synthesizing optically active glycidic acid which comprises causing 2-halo acid dehalogenase to act on an α,β-dihalopropionic acid under conditions where the pH exceeds 9; and a method of synthesizing optically active glycidic acid which comprises reacting the optically active β-halolactic acid obtained in the above manner with an alkali in a solvent.

The effects of the invention are far-reaching. Thus, optically active β-halolactic acids and optically active glycidic acid, which are important intermediates for drug synthesis, can be synthesized efficiently from inexpensive starting materials. The high production costs, low yields and complicated process steps encountered in the prior art enzymatic processes are avoided.

DETAILED DESCRIPTION OF THE INVENTION

As examples of the α,β-dihalopropionic acid used in accordance with the present invention, there may be mentioned α,β-dihalogenated propionic acids such as dichloropropionic acid, dibromopropionic acid and diiodopropionic acid which are commercially available.

The above halogenation products derived from inexpensive acrylic acid may also be used as starting materials in the practice of the invention.

The enzyme 2-halo acid dehalogenase used in accordance with the present invention includes enzymes generally classifiable under the class E.C. 3.8.1. which are capable of catalyzing dehalogenation at the α-position of halo-substituted carboxylic acids. Such enzymes can be obtained from fungi or bacteria, for example fungi belonging to the genus Trichoderma, Acrostalagmus, Penicillium or Cronostachys, or bacteria belong to the genus Pseudomonas, Arthrobacter, Rhizobium, Agrobacterium, Bacillus, Alcaligenes, Nocardia, Micrococcus, Achromobacter or Moraxella.

In particular, 2-halo acid dehalogenase derived from *Pseudomonas putida* 109 (deposited with the Fermentation Research Institute, Agency of Industrial Science and Technology under the deposit number FERM P-10262; after conversion to deposition under the Budapest Treaty, FERM BP-2631) acts on only L-form of α,β-halopropionic acid, has high specificity and is very effective (hereinafter, referred to as "L-2-halo acid dehalogenase"). This strain was isolated from a dry field farming soil sample collected in Uji City, Kyoto, Japan by enrichment culture in test tubes using a medium containing 0.3 w/v % α-chloropropionic acid as a single carbon source together with 0.5 w/v % ammonium sulfate, 0.1 w/v % monopotassium phosphate and 0.1 w/v % disodium phosphate dodecahydrate (pH 7.0). 2-Halo acid dehalogenase derived from Pseudomonas sp. UK 113 (deposited with the Fermentation Research Institute, Agency of Industrial Science and Technology under the deposit number FERM P-5666; after conversion to deposition under the Budapest Treaty, FERM BP-2626) has a property of acting on both D-form and L-form of α,β-dihalopropionic acids (hereinafter, referred to as "D,L-2-halo acid dehalogenase"). This UK 113 strain was also isolated in the same manner as in the above 109 strain.

In one embodiment of the invention, an optically active β-halolactic acid, particularly D-β-halolactic acid, can be synthesized, for example, by dissolving an α,β-dihalopropionic acid in a buffer and mixing this solution with L-2-halo acid dehalogenase, or bacterial or fungal cells containing L-2-halo acid dehalogenase, preferably in an amount of 10 units/g wet cell or more. Suitable buffers are, for instance, citrate, acetate, phosphate, Tris, imidazole, collidine, barbital, carbonate and borate buffers at a concentration of 10 to 500 mM, preferably 20 to 200 mM.

The α,β-dihalopropionic acid concentration (mM) is suitably within the range of 0.1 to 1,000, preferably 10 to 500, more preferably 50 to 300.

The quantity of L-2-halo acid dehalogenase required may vary depending on the quantity of α,β-dihalopropionic acid and on the time allowed for completion of the reaction. For conversion of 100 millimoles of an α,β-dihalopropionic acid to the corresponding D-β-haloactic acid in 8 hours, for instance, about 210 units of L-2-halo acid dehalogenase will be sufficient. In order to shorten the reaction time, an amount of the enzymes used will be increased in inverse proportion to the reaction time. The "1 unit" used herein means an amount of enzyme used for conversion of from 1 μmole of α,β-dichloropropionic acid to β-chlorolactic acid for a period of time of 1 minute at 30° C., which can be measured by the conventional method.

When the reaction is carried out under conditions such that the pH exceeds 9, glycidic acid is accumulated together with the β-halolactic acid. Therefore, it is preferable to adjust the pH to a level not higher than 9, more preferably within the range of 7 to 9, for example using a pH-stat. It is suitable to carry out the reaction at a temperature of 10° C. to 70° C., preferably 20° C. to 50° C., more preferably 30° C. to 40° C.

In this way, a D-β-halolactic acid-containing aqueous solution is obtained. The D-β-halolactic acid can be isolated from the aqueous solution, for example, by adjusting the pH of the D-β-halolactic acid-containing aqueous solution to the range of 1 to 4, adding, if necessary, an inorganic salt such as sodium chloride, potassium chloride, magnesium chloride, sodium nitrate or potassium bromide until saturation, extracting D-β-halolactic acid from the aqueous solution with a water-immiscible organic solvent such as ethyl acetate, ether, methylene chloride, chloroform or methyl propionate in the conventional manner, and drying and concentrating the extract in the conventional manner to give the D-β-halolactic acid as a solid.

Optically active glycidic acid, particularly D-glycidic acid, can be synthesized in one step, for example, by following the same procedure as described above for D-β-halolactic acid synthesis except that the pH of the reaction system is adjusted to a level above 9, preferably 9.5 to 11. It is also possible, for increasing the rate of conversion to glycidic acid, to carry out the process in two steps. Thus, in the first step, optically active β-halolactic acid is obtained from α,β-dihalopropionic acid in the manner mentioned above, and in the second step, the resulting optically active β-halolactic acid is converted to optically active glycidic acid in the manner mentioned below. That is, in the second step operation, optically active D-glycidic acid can be obtained by reacting an optically active D-β-halolactic acid isolated as a solid in the manner mentioned above with an alkali, such as potassium hydroxide, sodium hydroxide or lithium hydroxide, in an appropriate solvent, such as an alcohol (e.g., methanol, ethanol), an amide (e.g., dimethyl-formamide (DMF)) or dimethyl sulfoxide (DMSO). The conversion reaction of β-halolactic acid to glycidic acid is carried out by the conventional techniques as described, for example, in N. F. Blau, J. W. Johnson and C. G. struckwish J. Am. Chem. Soc., 76, 5106-5107 (1954).

The alkali concentration employed in the above reaction should suitably by within the range of 0.1 to 20 moles per liter, preferably 0.5 to 10 moles per liter of the solvent, more preferably 1 to 5 moles per liter of the solvent.

The D-β-halolactic acid may be added to the reaction system continuously, dropwise, or all at once. The temperature on that occasion should suitably be within the range of −50° C. to 30° C., preferably −30° C. to 10° C., more preferably −20° C. to 0° C. After completion of the β-halolactic acid addition, the temperature should suitably be maintained within the range of −30° C. to 50° C., preferably −20° C. to 30° C., more preferably −5° C. to 20° C.

The reaction mixture thus obtained is filtered in the conventional manner. The supernatant contains the desired, optically active D-glycidic acid.

In the practice of the invention, it is also possible to synthesize L-β-halolactic acid and L-glycidic acid, or to separately synthesize the L-form and D-form of a β-halolactic acid, or the L-form and D-form of glycidic acid, for example, by the following methods.

Thus, an α,β-dihalopropionic acid in racemic form is used as the starting material and the corresponding β-halolactic acid in the optically active D-form or glycidic acid in the optically active D-form is first synthesized by using L-2-halo acid dehalogenase derived from *Pseudomonas putida* 109 which acts on the conversion of α,β-dihalopropionic acids in L-form alone. The optically active D-form of a β-halolactic acid, the optically active D-form of glycidic acid and the unreacted α,β-dihalopropionic acid are separated from the reaction solution in the conventional manner, for example using an anion exchange resin such as Dowex 1, Dowex WSG, Dowex MWA-1, Amberlite IRA-410, Amberlite IRA-45, DEAE-Cellulose, DEAE-Sephacel, etc. For instance, when Amberlite IRA-45 is used, D-β-halolactic acid is first eluted with 0.1 NHCl, and then D-α,β-dihalopropionic acid is eluted. Then D,L-2-halo acid dehalogenase derived from Pseudomonas sp. UK 113 which acts on the conversion of α,β-dihalopropionic acids in both D- and L-forms is added to the D-form of the α,β-dihalopropionic acid separated under the same condition as in the case of preparing D-β-halolactic acid using L-2-halo acid dehalogenase, whereby the optically active L-form of the β-halolactic acid or glycidic acid can be obtained.

In the practice of the invention, L-2-halo acid dehalogenase and D,L-2-halo acid dehalogenase may be used in the form of a purified enzyme, a crude enzyme solution or microbial cells containing the same. It is also possible to use the enzyme in the form of an enzyme immobilized on a macromolecular carrier or in the crosslinked, water-insoluble form, as described, for example, in U.S. Pat. Nos. 4,797,358, 4,794,083 and 4,783,409. As suitable examples of the macromolecular carrier, there may be mentioned gelatin, polysaccharides and derivatives thereof, such as cellulose, dextran and agarose, vinyl polymers and derivatives thereof, such as polystyrene, ethylene-maleic acid copolymers and cross-linked acrylic polymers, polyamino acids or polyamide derivatives, such as L-alanine-L-glutamic acid copolymers and polyaspartic acid, and inorganic materials, such as glass, alumina, hydroxyapatite and Celite. The enzyme may be bound to, included in or adsorbed on such macromolecular carriers.

For crosslinking, a divalent reagent, such as glutaraldehyde, diisocyanates (e.g., hexamethylene diisocyanate, toluene diisocyanate or hexamethylene diisothiocyanate) or bisazobenzidine, is admixed with the enzyme in purified, crude solution or microbial cell form as described, for example in U.S. Pat. No. 4,798,793, and the crosslinking reaction is allowed to proceed.

The immobilized or crosslinked form of enzyme such as mentioned above can be used repeatedly for the intended synthesis and, furthermore, it makes it possible to conduct the process not only batchwise but also continuously in a column. Particularly, when a column is used, an optically active β-halolactic acid or optically active glycidic acid can be synthesized continuously with great advantage. In this case, the above batch conditions can be also applied to the continuous processing and the starting material solution may be fed to the column either at the top or at the bottom thereof. The rate of flow may vary depending on the column size and the packing (immobilized or crosslinked enzyme or cells). In a typical example in which a 500 cc column is packed with microbial cells immobilized and crosslinked by means of gelatin and glutaraldehyde, the flow rate should suitably be within the range of 0.5 ml to 20 ml per minute, preferably 1 to 10 ml per minute, more preferably 2 to 5 ml per minute.

The following examples are further illustrative of the present invention.

EXAMPLE 1

Twenty liters of an aqueous medium containing 0.5% (% by weight; hereinafter the same shall apply) ammonium sulfate, 0.1% monopotassium phosphate, 0.1% disodium phosphate, 0.01% magnesium sulfate, 0.0005% ferrous sulfate, 0.0005% calcium hydroxide, 0.0001% manganese sulfate, 0.0001% sodium molybdate and 0.3% α,β-dichloropropionic acid and adjusted to pH 7.0 was inoculated with *Pseudomonas putida* 109 (FERM BP-2631) (about 2 g wet cell) and cultivation was carried out at 30° C. for about 50 hours.

Cells thus grown were harvested by centrifugation (8,000 rpm) for 15 minutes and disrupted by sonication (insonator model 200M, manufactured by KUBOTA, Ltd., 1.5A) for 10 minutes. To the resultant fluid was added ammonium sulfate until 40% saturation. The precipitate was then removed. Ammonium sulfate was further added to the supernatant until 70% saturation. The resultant precipitate was recovered and dissolved in 25 mM potassium phosphate buffer (pH 7.5). The solution was dialyzed for 12 hours and then applied to a DEAE-Sephacel column (6×50 cm; manufactured by Pharmacia). Development/elution was carried out using phosphate buffer (pH 7.5) while varying the phosphate concentration from 50 mM to 500 mM in accordance with a linear gradient elution method. Active eluate fractions were combined, ammonium sulfate was added until 70% saturation, and the precipitate was collected, dialyzed against phosphate buffer (pH 7.5) in a concentration of 50 mM for 12 hours and applied to a hydroxyapatite column (Biogel HR ®, manufactured by Bio-Rad, column size:4 cmφ×35 cm) pre-equilibrated with 5 mM potassium phosphate buffer (pH 7.5). Development/elution was carried out with 5 mM to 100 mM phosphate buffer in accordance with a linear gradient elution method. Active fractions were combined and subjected to fractionation with ammonium sulfate in the same manner as mentioned above. Further, the active fractions were applied to a Sephadex G-150 column (3×130 cm; manufactured by Pharmacia) pre-equilibrated with 50 mM potassium phosphate buffer (pH 7.5), and eluted with the same buffer to give purified L-2-halo acid dehalogenase.

Twenty units of the thus-purified enzyme were added to 30 ml of 50 mM carbonate buffer (pH 8.5) containing 10 mg of α,β-dichloropropionic acid (racemic form), and the enzymatic reaction was allowed to proceed at 30° C. for 10 hours. The reaction mixture was subjected to ultrafiltration for enzyme recovery, the filtrate was adjusted to pH about 1 with hydrochloric acid, sodium chloride was added until saturation, and the resultant mixture was extracted with three 300 ml portions of ethyl acetate. The extracts were combined, dried over sodium sulfate and then concentrated to dryness. The residue was recrystallized from a 1:9 (by volume) mixture of toluene and benzene to give 2.8 mg of D-β-chlorolactic acid as white needles.

Elemental analysis of these crystals gave the following results: C, 28.93%; H, 4.00%; Cl, 28.44%. When calculated on the assumption that half of the racemic α,β-dichloropropionic acid used had been in the L- form, the yield of D-β-chlorolactic acid amounted to 64%. Fractional determination of the above crystals using D-lactate dehydrogenase and L-lactate dehydrogenase revealed that the D-β-chlorolactic acid had an optical purity of 94% as calculated as follows:

*Optical purity (%)* = [(*D-β-chlorolactic acid* − *L-β-chlorolactic acid*)/(*D-β-chloroacetic acid* + *L-β-chlorolactic acid*)] × 100

EXAMPLE 2

A flat membrane-type ultrafiltration vessel (manufactured by Millipore) was connected, via tubes, to two inlets of a three-necked, glass enzymatic reaction vessel (capacity 150 ml). This system was charged with 150 ml of 50 mM Tris sulfate buffer (pH 8.5), which was circulated at a rate of 5 liters per hour, while the reaction vessel was maintained at 30° C. on a water bath.

L-2-Halo acid dehalogenase (100 units) purified as described in Example 1 was added to the reaction vessel through the third inlet. The third inlet was further fitted with a tube and a 500 mM solution of α,β-dichloropropionic acid (racemic form) dissolved in 3.5 l of the same buffer as the circulating buffer and stored at 4° C. was fed to the reactor through the tube at a flow rate of 50 cc per hour.

The D-β-chlorolactic acid-containing solution that had passed through the ultrafiltration membrane was continuously recovered at a rate of 50 cc per hour and stored at 4° C. This reaction was carried out for about 3 days, whereby 3.2 liters of a D-β-chlorolactic acid-containing solution was obtained. This solution was adjusted to pH 1 with hydrochloric acid, sodium chloride was then added until saturation, the resulting mixture was extracted with several portions of ethyl acetate (5 liters in total), and the whole extract was dried over sodium sulfate and concentrated to dryness to give crude D-β-chlorolactic acid. This crude D-β-chlorolactic acid was recrystallized from benzene to give 82 g of D-β-chlorolactic acid as white needles.

Elemental analysis of the crystals gave the following results: C, 28.91%; H, 4.06%; Cl 28.50%. The optical purity of the product D-β-chlorolactic acid was estimated by reacting the same with methanol for methylation, then reacting with MTPA chloride reagent for conversion to an MTPA derivative and subjecting the derivative to $^1$H NMR spectrometry. As a result, the optical purity was found to be 96%.

A 50 gram portion of the D-β-chlorolactic acid obtained by the above procedure above was dissolved in 100 ml of methanol and the solution was slowly added dropwise to a solution of 50 g of KOH in 500 ml of methanol in a flask. This procedure was conducted under ice cooling so that the temperature could not exceed 10° C.

After completion of the dropping, the mixture was stirred at room temperature (25° C.) for about 3 hours. The resulting potassium chloride was removed by filtration. After removal of the methanol and washing with ice-cooled methanol, there was obtained 40.2 g of potassium D-glycidate. The yield was 91%.

The optical purity of the potassium D-glycidate was determined by the same derivatization as above followed by $^1$H NMR spectrometry and found to be 88%.

EXAMPLE 3

The bacterial strain Pseudomonas UK 113 (FERM BP-2626) was inoculated into 20 liters of an aqueous medium containing 0.3% D,L-α,β-dichloropropionic acid, 0.5% ammonium sulfate, 0.1% monopotassium phosphate, 0.1% disodium phosphate and 0.01% magnesium sulfate and adjusted to pH 7.0 and cultivated at 30° C. for about 50 hours.

The cells which grew were harvested by centrifugation (8,000 rpm) for 15 minutes and disrupted in a Dyno mill (Type KDL Willy A. Bachofen, manufactured by Engineers, glass bead size: 0.10 to 0.20 mmφ) for 5 minutes to give a crude enzyme solution. D,L-2-Halo acid dehalogenase was then purified from the crude enzyme solution in the same manner as in Example 1.

D,L-α,β-Dichloropropionic acid (0.05 mole) was dissolved in 100 ml of 50 mM Tris-hydrochloride buffer (pH 8.5). To the resulting solution there was first added 60 units of L-2-halo acid dehalogenase purified as in Example 1 and the reaction was carried out at 30° C. for 24 hours while the pH was maintained at 8.5 with 5N NaOH using a pH-stat.

The pH was then lowered to 2 with hydrochloric acid and the reaction mixture was concentrated using an evaporator in the conventional manner. D-α,β-Dichloropropionic acid and D-β-chlorolactic acid were extracted from the concentrate with ethyl acetate in the conventional manner. After the removal of ethyl acetate using an evaporator in the conventional manner, the remaining solution was applied to a formic acid-equilibrated Dowex 1 (manufactured by Muromachi Kagaku Kogyo) column (5.0×50 cm). D-β-Chlorolactic acid was eluted with 0.5M formic acid and then D-α,β-dichloropropionic acid with 2M formic acid. The formic acid was removed from each eluate fraction using an evaporator in the conventional manner.

The thus-concentrated D-α,β-dichloropropionic acid was diluted about 30-fold using Tris-hydrochloride buffer (pH 8.5), the dilution was adjusted to pH 8.5 using sodium hydroxide, 60 units of D,L-2-halo acid dehalogenase was added, and the reaction was carried out for 24 hours in the same manner as described above. The reaction mixture was then adjusted to pH 2 with hydrochloric acid and evaporated to dryness using an evaporator in the conventional manner. L-β-Chlorolactic acid was extracted from the dried solid with ethyl acetate in the conventional manner.

The thus-obtained D-β-chlorolactic acid and L-β-chlorolactic acid were respectively recrystallized from benzene to give 2.86 mg (23 millimole) of D-β-chlorolactic acid and 2.24 mg (18 millimole) of L-β-chlorolactic acid. Elemental analysis of the product D-β-chlorolactic acid gave the following results: C, 28.92%; H, 3.99%; Cl, 28.45%. The results of elemental analysis of the L-β-chlorolactic acid were as follows: C, 28.93%; H, 4.01%; Cl, 28.42%.

The yield of D-β-chlorolactic acid was 92% and that of L-β-chlorolactic acid was 72%. The optical purity of the D-β-chlorolactic acid was 97% and that of the L-β-chlorolactic acid was 92%.

Then, 2 mg of the D-β-chlorolactic acid obtained by the above method was dissolved in 0.5 ml of methanol containing 0.1 g of KOH with ice cooling, the ice cooling was then discontinued and the mixture was stirred at room temperature (25° C.) for three hours.

The resulting potassium chloride was removed by centrifugation, the methanol was then removed, and the washing with methanol cooled to about 0° C. was conducted. Potassium D-glycidate was thus obtained.

The L-β-chlorolactic acid was also converted to potassium L-glycidate in the same manner.

The yield of potassium D-glycidate and that of potassium L-glycidate were 95% and 96%, respectively. The same derivatization as in Example 2 and the subsequent $^1$H NMR spectrometry revealed that the products potassium D-glycidate and potassium L-glycidate had optical purities of 90% and 87%, respectively.

EXAMPLE 4

A 10% gelatin solution (10 ml) was added to 60 g of wet cells of *Pseudomonas putida* 109 (FERM BP-2631). The mixture was kneaded and strained through wire guaze. The granular cell mass was immersed in 5% glutaraldehyde at 25° C. for 4 hours, then washed thoroughly with water and packed into a column (20 mm in diameter, 250 mm in length).

Then, 300 ml of borate buffer (pH 9.5) containing 5 g of α,β-dibromopropionic acid (racemic form) was passed through the column at a flow rate of 2 ml/minute. The column was maintained at a constant temperature by feeding warm water (40° C.) to the jacket of the column. The resulting eluate fractions were combined and adjusted to a pH of about 4 with hydrochloric acid. The resultant precipitate was filtered off and 270 ml of the filtrate was applied to a column (diameter 30 mm, length 500 mm) of an anion exchange resin (Dowex 1; manufactured by Muromachi Kagaku Kogyo) equilibrated with 50 mM sodium acetate buffer (pH 4). The optically active D-glycidic acid thus adsorbed was eluted with the same buffer on a sodium chloride concentration gradient obtained by varying the sodium chloride concentration from 0 mM to 100 mM in 50 mM sodium acetate buffer. Ether was added the resulting D-glycidic acid fraction and extraction was effected. Concentration to dryness of the extract gave D-glycidic acid.

Elemental analysis of the product D-glycidic acid gave the following results: C, 32.68%; H, 2.74%; K, 35.52%. The yield was 82% calculated on the assumption that half of the starting α,β-dibromopropionic acid was L-α,β-dibromopropionic acid. The optical purity determined by the same derivatization as in Example 2 and $^1$H NMR spectroscopy was 87%.

While the invention has been described in detail and with reference to specific embodiments thereof, it will be apparent to one skilled in the art that various changes and modifications can be made therein without departing from the spirit and scope thereof.

What is claimed is:

1. A method of synthesizing an optically active β-halolactic acid which comprises contacting an α,β-dihalopropionic acid with 2-halo acid dehalogenase, under conditions such that the pH is 9 or less.

2. A method as claimed in claim 1, wherein said 2-halo acid dehalogenase is L-2-halo acid dehalogenase.

3. A method as claimed in claim 1, wherein said α,β-dihalopropionic acid is α,β-dichloropropionic acid, α,β-dibromopropionic acid or α,β-diiodopropionic acid.

4. A method as claimed in claim 1, wherein said 2-halo acid dehalogenase is of the bacterial or fungal origin.

5. A method as claimed in claim 1, wherein said 2-halo acid dehalogenase is derived from *Pseudomonas putida* 109 or Pseudomonas sp. UK 113.

6. A method as claimed in claim 1, wherein said 2-halo acid dehalogenase is in the form of purified enzyme, crude enzyme solution, enzyme-containing microbial cells or is immobilized on a macromolecular carrier.

7. A method as claimed in claim 1, wherein the enzymatic reaction is carried out in a buffer at an α,β-dihalopropionic acid concentration of 0.1 to 1,000 mM.

8. A method as claimed in claim 1, wherein the enzymatic reaction is carried out using a column containing 2-halo acid dehalogenase in an immobilized or cross-linked form.

9. A process of synthesizing an optically active β-halolactic acid in D-form and an optically active β-halolactic acid in L-form which comprises:

(a) reacting an α,β-dihalopropionic acid in racemic form with L-2-halo acid dehalogenase to convert an α,β-dihalopropionic acid in L-form to β-halolactic acid in D-form, under conditions such that the pH is 9 or less;

(b) separating both the resulting β-halolactic acid in D-form and an unreacted α,β-dihalopropionic acid in D-form, from the reaction mixture; and (c) reacting the resulting α,β-dihalopropionic acid in D-form with D,L-2-halo acid dehalogenase to synthesize a β-halolactic acid in L-form, under conditions such that the pH is 9 or less.

* * * * *